United States Patent
Borgaonkar et al.

(10) Patent No.: US 9,474,610 B2
(45) Date of Patent: Oct. 25, 2016

(54) ADJUSTABLE LENGTH REAR TIP EXTENDER FOR PENILE PROSTHESIS

(75) Inventors: Harshad M. Borgaonkar, Blaine, MN (US); Randall H. Zauner, Stillwater, MN (US); Christopher A. Wilhoit, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 790 days.

(21) Appl. No.: 13/332,660

(22) Filed: Dec. 21, 2011

(65) Prior Publication Data

US 2012/0157764 A1    Jun. 21, 2012

Related U.S. Application Data

(60) Provisional application No. 61/425,395, filed on Dec. 21, 2010.

(51) Int. Cl.
    *A61F 2/26*    (2006.01)

(52) U.S. Cl.
    CPC .......... *A61F 2/26* (2013.01); *A61F 2250/0003* (2013.01); *A61F 2250/0007* (2013.01)

(58) Field of Classification Search
    CPC ............ A61F 2/26; A61F 5/41; A61H 19/00
    USPC ...................................... 600/38–41
    See application file for complete search history.

(56) References Cited

U.S. PATENT DOCUMENTS

| | | |
|---|---|---|
| 3,853,122 A | 12/1974 | Strauch et al. |
| 3,954,102 A | 5/1976 | Buuck |
| 4,009,711 A | 3/1977 | Uson |
| 4,201,202 A | 5/1980 | Finney et al. |
| 4,204,530 A | 5/1980 | Finney |
| 4,222,377 A | 9/1980 | Burton |
| 4,224,934 A | 9/1980 | Scott et al. |
| 4,235,227 A | 11/1980 | Yamanaka |
| 4,267,829 A | 5/1981 | Burton et al. |
| 4,318,396 A | 3/1982 | Finney |
| 4,342,308 A | 8/1982 | Trick |
| 4,353,360 A | 10/1982 | Finney et al. |
| 4,360,010 A | 11/1982 | Finney |
| 4,364,379 A | 12/1982 | Finney |
| 4,369,771 A | 1/1983 | Trick |
| 4,378,792 A | 4/1983 | Finney |

(Continued)

FOREIGN PATENT DOCUMENTS

| | | |
|---|---|---|
| WO | WO02/38079 | 5/2002 |
| WO | WO03/096929 | 11/2003 |

OTHER PUBLICATIONS

Gregory, John G. et al., The Inflatable Penile Prosthesis: Failure of the Rear Tip Extender in Reducing the Incidence of Cylinder Leakage, The Journal of Urology, vol. 131, pp. 668-669 (Apr. 1984).

(Continued)

*Primary Examiner* — Samuel Gilbert
(74) *Attorney, Agent, or Firm* — Brake Hughes Bellermann LLP

(57) ABSTRACT

An implantable penile prosthesis having an adjustable length rear tip extender. The extender is connectable with at least one inflatable cylinder. The adjustable length rear tip extender can be telescoping, or include one or more segments capable of being cut away or otherwise removed, to adjust the effective length for the at least one inflatable cylinder.

9 Claims, 4 Drawing Sheets

(56) References Cited

U.S. PATENT DOCUMENTS

| | | | |
|---|---|---|---|
| 4,383,525 A | 5/1983 | Scott et al. | |
| 4,399,811 A | 8/1983 | Finney et al. | |
| 4,399,812 A | 8/1983 | Whitehead | |
| 4,404,968 A | 9/1983 | Evans, Sr. | |
| 4,407,278 A | 10/1983 | Burton et al. | |
| 4,412,530 A | 11/1983 | Burton | |
| 4,424,807 A | 1/1984 | Evans, Sr. | |
| 4,441,491 A | 4/1984 | Evans, Sr. | |
| 4,449,520 A | 5/1984 | Palomar | |
| 4,449,521 A * | 5/1984 | Panzer | 600/39 |
| 4,457,335 A | 7/1984 | Trick | |
| 4,523,584 A | 6/1985 | Yachia et al. | |
| 4,532,920 A | 8/1985 | Finney | |
| 4,550,719 A | 11/1985 | Finney et al. | |
| 4,550,720 A | 11/1985 | Trick | |
| 4,558,693 A | 12/1985 | Lash et al. | |
| 4,559,931 A | 12/1985 | Fischell | |
| 4,566,446 A | 1/1986 | Fogarty | |
| 4,572,168 A | 2/1986 | Fischell | |
| 4,574,792 A | 3/1986 | Trick | |
| 4,590,927 A | 5/1986 | Porter et al. | |
| 4,596,242 A | 6/1986 | Fischell | |
| 4,602,621 A * | 7/1986 | Hakky | 600/40 |
| 4,602,625 A | 7/1986 | Yachia et al. | |
| 4,604,994 A | 8/1986 | Sealfon | |
| 4,611,584 A | 9/1986 | Finney | |
| 4,622,958 A | 11/1986 | Finney | |
| 4,651,721 A | 3/1987 | Mikulich et al. | |
| 4,653,485 A | 3/1987 | Fishell | |
| 4,664,100 A | 5/1987 | Rudloff | |
| 4,665,903 A | 5/1987 | Whitehead | |
| 4,671,261 A | 6/1987 | Fischell | |
| 4,682,583 A | 7/1987 | Burton et al. | |
| 4,682,589 A | 7/1987 | Finney | |
| 4,718,410 A | 1/1988 | Hakky | |
| 4,724,830 A | 2/1988 | Fischell | |
| 4,726,360 A | 2/1988 | Trick et al. | |
| 4,730,607 A | 3/1988 | Fischell | |
| 4,766,889 A | 8/1988 | Trick et al. | |
| 4,773,403 A | 9/1988 | Daly | |
| 4,782,826 A | 11/1988 | Fogarty | |
| 4,790,298 A | 12/1988 | Trick | |
| 4,791,917 A | 12/1988 | Finney | |
| 4,807,608 A | 2/1989 | Levius | |
| 4,829,990 A | 5/1989 | Thuroff et al. | |
| 4,881,530 A | 11/1989 | Frick | |
| 4,895,139 A | 1/1990 | Hauschild et al. | |
| 4,917,110 A | 4/1990 | Trick | |
| 4,988,357 A | 1/1991 | Koss | |
| 5,010,882 A * | 4/1991 | Polyak et al. | 600/40 |
| 5,048,510 A | 9/1991 | Hauschild et al. | |
| 5,062,416 A | 11/1991 | Stucks | |
| 5,062,417 A | 11/1991 | Cowen | |
| 5,063,914 A * | 11/1991 | Cowen | 600/40 |
| 5,067,485 A | 11/1991 | Cowen | |
| 5,101,813 A | 4/1992 | Trick | |
| 5,112,295 A | 5/1992 | Zinner et al. | |
| 5,114,398 A | 5/1992 | Trick et al. | |
| 5,129,880 A | 7/1992 | Grundei | |
| 5,141,509 A | 8/1992 | Burton et al. | |
| 5,167,611 A | 12/1992 | Cowan | |
| 5,171,272 A | 12/1992 | Levius | |
| 5,250,020 A | 10/1993 | Bley | |
| 5,263,981 A * | 11/1993 | Polyak et al. | 623/23.67 |
| 5,344,388 A | 9/1994 | Maxwell et al. | |
| 5,433,694 A | 7/1995 | Lim | |
| 5,704,895 A | 1/1998 | Scott et al. | |
| 5,851,176 A | 12/1998 | Willard | |
| 5,895,424 A | 4/1999 | Steele, Sr. et al. | |
| 6,387,071 B1 | 5/2002 | Constantz | |
| 6,443,887 B1 | 9/2002 | Derus et al. | |
| 6,533,719 B2 | 3/2003 | Kuyava et al. | |
| 6,558,315 B1 | 5/2003 | Kuyava | |
| 6,592,515 B2 | 7/2003 | Thierfelder et al. | |
| 6,723,042 B2 | 4/2004 | Almli et al. | |
| 6,730,017 B2 | 5/2004 | Henkel et al. | |
| 6,733,527 B2 | 5/2004 | Koyfman | |
| 6,808,489 B2 * | 10/2004 | George et al. | 600/40 |
| 6,911,003 B2 | 6/2005 | Anderson et al. | |
| 6,929,599 B2 | 8/2005 | Westrum, Jr. | |
| 6,935,847 B2 | 8/2005 | Kuyava et al. | |
| 6,991,601 B2 | 1/2006 | Kuyava et al. | |
| 7,066,877 B2 | 6/2006 | Kuyava | |
| 7,066,878 B2 | 6/2006 | Eid | |
| 7,131,944 B2 | 11/2006 | Jacquetin | |
| 7,169,103 B2 | 1/2007 | Ling et al. | |
| 7,244,227 B2 | 7/2007 | Morningstar | |
| 7,250,026 B2 | 7/2007 | Kuyava | |
| 7,276,040 B2 * | 10/2007 | Gomez-de-Diego | 602/36 |
| 7,350,538 B2 | 4/2008 | Kuyava et al. | |
| 7,390,296 B2 | 6/2008 | Mische | |
| 7,393,320 B2 | 7/2008 | Montpetit et al. | |
| 7,407,480 B2 | 8/2008 | Staskin et al. | |
| 7,438,682 B2 | 10/2008 | Henkel et al. | |
| 7,491,164 B2 | 2/2009 | Choi et al. | |
| 7,494,495 B2 | 2/2009 | Delorme et al. | |
| 7,637,861 B2 | 12/2009 | Kuyava et al. | |
| 7,901,346 B2 | 3/2011 | Kovac et al. | |
| 8,052,593 B2 * | 11/2011 | Jahns et al. | 600/40 |
| 2002/0033564 A1 | 3/2002 | Koyfman | |
| 2002/0082473 A1 | 6/2002 | Henkel et al. | |
| 2002/0082709 A1 | 6/2002 | Almli et al. | |
| 2002/0091302 A1 | 7/2002 | Kuyava et al. | |
| 2002/0103542 A1 | 8/2002 | Bilbo | |
| 2003/0028076 A1 | 2/2003 | Kuyava et al. | |
| 2003/0176762 A1 | 9/2003 | Kammerer | |
| 2003/0220538 A1 | 11/2003 | Jacquetin | |
| 2004/0039453 A1 | 2/2004 | Anderson et al. | |
| 2004/0116774 A1 | 6/2004 | Migliari | |
| 2004/0220447 A1 | 11/2004 | Morningstar | |
| 2004/0249397 A1 | 12/2004 | Delorme et al. | |
| 2004/0249473 A1 | 12/2004 | Delorme et al. | |
| 2005/0080317 A1 | 4/2005 | Merade | |
| 2005/0245787 A1 | 11/2005 | Cox et al. | |
| 2005/0250977 A1 | 11/2005 | Montpetit et al. | |
| 2005/0267325 A1 | 12/2005 | Bouchier et al. | |
| 2006/0130848 A1 | 6/2006 | Carey | |
| 2006/0235267 A1 | 10/2006 | George et al. | |
| 2008/0114202 A1 | 5/2008 | Kuyava et al. | |
| 2009/0012353 A1 | 1/2009 | Beyer | |
| 2009/0105530 A1 | 4/2009 | Kuyava | |
| 2009/0124851 A1 | 5/2009 | Kuyava et al. | |
| 2009/0287042 A1 | 11/2009 | Almli et al. | |

OTHER PUBLICATIONS

Hellstrom, WJG, Three-Piece INFLATABL4E Penile Prosthesis Components (Surgical Pearls on Reservoirs, Pumps, and Rear-Tip Extenders), Int'l J of Impotence Research, vol. 15. Suppl 5, pp. S136-S138 (2003).

Joseph, David et al., Bilateral Dislocation of Rear Tip Extenders From the Inflatable Penile Prosthesis, The Journal of Urology, vol. 1128, pp. 1317-1318 (Dec. 1982).

Kim, Sae-Chul, M.D., Mechanical Reliability of AMS Hydraulic Penile Prostheses, Journal of Korean Medical Science, vol. 10. No. 6, pp. 422-425 (Dec. 1995).

Levine, Laurence A. et al., Mechanical Reliability and Safety of, and Patient Satisfaction With the Ambicor Inflatable Penile Prosthesis: Results of a 2 Center Study, The Journal of Urology, vol. 166, pp. 932-937 (Sep. 2001).

Malloy, Terrance R. et al., Improved Mechanical Survival With Revised Model Inflatable Penile Prosthesis Using Rear-Tip Extenders, The Journal of Urology, vol. 128, pp. 489-491 (Sep. 1982).

Montague, Drogo K., Experience With Semirigid Rod and Inflatable Penile Prosthesis, The Journal of Urology, vol. 129, pp. 967-968 (May 1983).

Mooreville, Michael et al., Implantation of Inflatable Penile Prosthesis in Patients With Severe Corporeal Fibrosis: Introduction of a New Penile Cavernotome, The Journal of Urology, vol. 162, pp. 2054-2057 (Dec. 1999).

(56) References Cited

OTHER PUBLICATIONS

Mulcahy, John J., Distal Corporplasty for Lateral Extrusion of Penile Cylinders, The Journal of Urology, vol. 161, pp. 193-195 (Jan. 1999).

Parulkar, B.G. et al., Revision Surgery for Penile Implants, Int. J. Impotence Res., vol. 6, pp. 17-23 (1994).

Randrup, Eduardo R., M.D., Penile Implant Surgery: Rear Tip Extender That Stays BE3HIND, Urology, vol. XXXIX, No. 1, pp. 667-669 (Jan. 1992).

Stein, Avi et al., Malleable Penile Prosthesis Removal Leaving Behind the Rear Tip Extenders: A Clinical Presentation, Urol. Intl, 50, pp. 119-120 (1993).

AMS 700.TM. Inflatable Penile Prosthesis Product Line, Inservice Script brochure, American Medical Systems (1992).

Ultrex/Ultrex Plus brochure, American Medical Systems, Inc. (1998).

Description of Ultrex Fabric and Yarns (Mar. 30, 2001).

Mentor Alpha.RTM. Inflatable Penile Prosthesis, Surgical Protocol, 15 pages. (1998).

Mentor Urology Products, 20 pages (May 1998).

Mentor Alpha.RTM., The Results Are In, 14 pages (Apr. 1997).

Mentor Alpha.RTM.Narrow Base, Simplifying Penile Implant Surgery by Making Difficult Cases More Manageable, 2 pages (Oct. 1996).

Mentor.RTM. Acu-Form.RTM. Penile Prosthesis, 2 pages (Aug. 1997).

Mentor.RTM. Acu-Form.RTM. Penile Prosthesis, Malleable Penile Prosthesis, Surgical Protocol, 8 pages (Sep. 1997).

\* cited by examiner

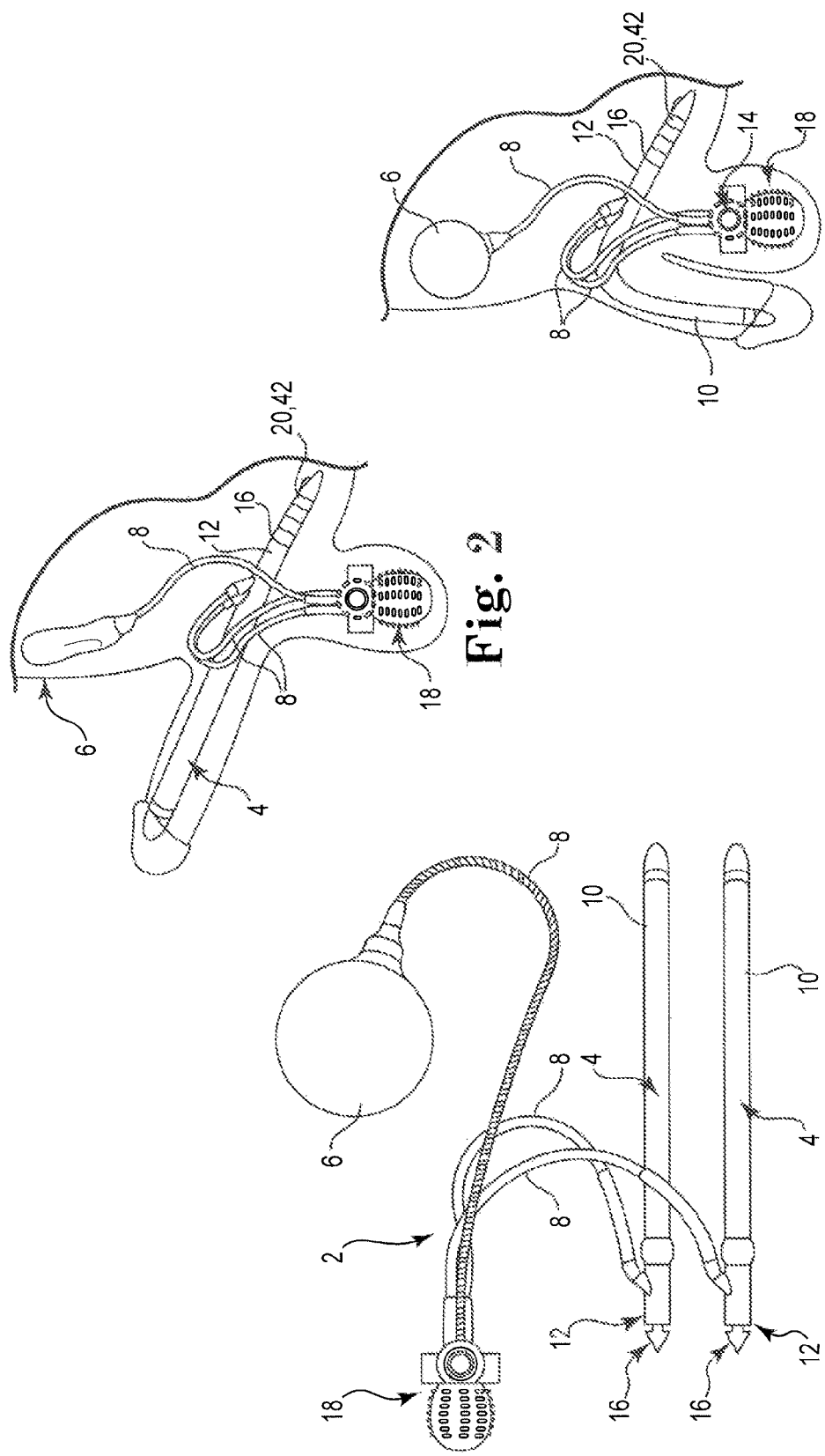

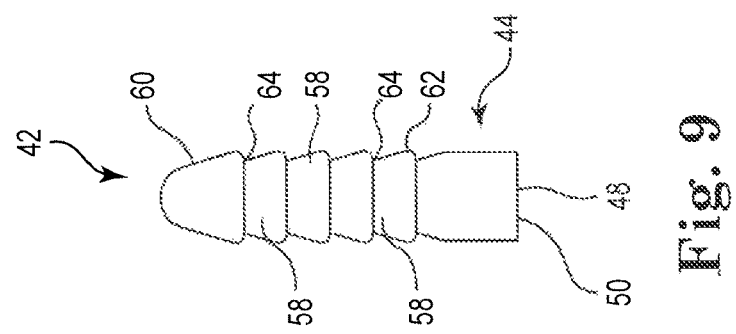
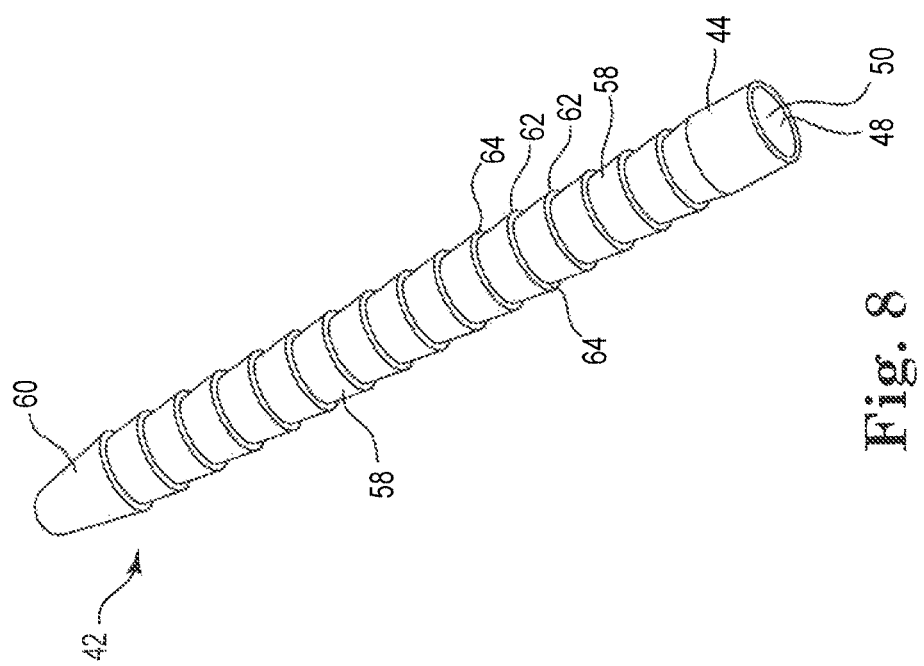

ADJUSTABLE LENGTH REAR TIP
EXTENDER FOR PENILE PROSTHESIS

PRIORITY

This application claims priority to and the benefit of U.S. Provisional Patent Application No. 61/425,395, filed Dec. 21, 2010, which is incorporated herein by reference in its entirety.

FIELD OF THE DISCLOSURE

The present invention is generally directed to an implantable penile prosthesis and, more specifically, to an inflatable cylinder to which a rear tip extender can be affixed, wherein the rear tip extender provides an adjustable effective length for the inflatable cylinder.

BACKGROUND OF THE DISCLOSURE

Erectile dysfunction is a psychological or physical disorder preventing males from forming or maintaining an erection during sexual intercourse. Erectile dysfunction is treatable through the implantation of a selectively inflatable penile prosthesis within the corpus cavernosum of the penis that mechanically erects the penis. Typically, an implantable penile prosthesis comprises at least one inflatable cylinder positioned within the corpus cavernosum and operably linked to an apparatus for selectively inflating the cylinder. Generally, a first and second inflatable cylinder is placed within the corpus cavernosum. A rear tip extender, as disclosed in U.S. Pat. No. 6,808,489 to George et al., which is incorporated by reference in its entirety, can be fitted to the rear tip of each inflatable cylinder to change the effective length of the inflatable cylinder according to the needs of the patient. A rear tip extender is often necessary to insure the implantable penile prosthesis is properly fitted and positioned within the penis according to the specific anatomy of the male patient.

Rear tip extenders typically comprise a molded polymer and, as a result, cannot be inflated or changed in size. As a result, implantable penile prosthesis are often provided with a plurality of rear tip extenders having a range of sizes from which a surgeon can select the appropriate size that best suits the patient's needs. The unused rear tip extenders are often discarded, creating a considerable amount of waste. While the unused rear tip extenders are often returned to the manufacturer, manufacturers are left with large inventories of rarely used "off-sizes" of rear tip extenders that are ultimately discarded. Similarly, as each rear tip extender is individually molded, each manufacturer must produce and maintain production molds corresponding to each rear tip extender size at a considerable cost to the manufacturer. Consequently, while providing a plurality of sizes of rear tip extenders insures a proper fit for the implantable penile prosthesis, doing so prevents manufacturers from mass producing implantable penile prosthesis having rear tip extenders in a cost efficient manner.

A related drawback of individually molding different sized rear tip extenders is that each tip extender is of a fixed size and cannot be adjusted to accommodate discrete sizes between the pre-molded sizes. An important consideration with implantable penile prosthesis is that the size and fit of the prosthesis must closely match the patient's needs to prevent patient discomfort during use. Consequently, the ideal size for a particular patient is often between one of the sizes of rear tip extender, which can cause patient discomfort.

SUMMARY OF THE DISCLOSURE

The present invention is directed to an implantable penile prosthesis having an adjustable length rear tip extender adapted to change the effective length of the implantable penile prosthesis. A single rear tip extender, according to embodiments of the present invention, can be selectively set at multiple lengths according to the needs of the patient. Unlike conventional rear tip extenders that are molded in a single length and must be interchanged with a different rear tip extender of a different molded length to change the overall length of the implantable penile prosthesis, the single adjustable length rear tip extender of the present invention can be provided to reduce waste and provide considerable cost in both manufacturing and storage/disposal. Further, the adjustable length rear tip extender of the present invention allows medical personnel to set the length of the rear tip extender at the most ideal length, and at the ideal time, for the patient rather than selecting from a set of rear tip extenders having predetermined lengths.

In certain embodiments of the present invention, the adjustable length rear tip extender can include a telescoping rear tip extender. The telescoping rear tip extender can generally comprise an interface segment, at least one telescoping segment, and a conical end segment. The interface segment can include a receiving port for receiving the mounting nub at the rear of an inflatable cylinder and operably linking the telescoping rear tip extender to the inflatable cylinder. Each telescoping segment generally includes a frustoconical shape and can be affixed together in an end-to-end configuration with other like telescoping segments to change the overall length of the rear tip. The conical end segment includes a conical shape and is adapted to be affixed to a telescoping segment such that the combined conical end segment and telescoping segment comprise a generally conical shape. The interface segment is affixable to the opposite end of a telescoping segment or series of telescoping segments from the conical end segment such that the telescoping rear tip defines a generally conical shape pointing outwardly from the end of an inflatable cylinder. According to an embodiment of the present invention, the interface segment and each of the telescoping segments defines an internal lumen for receiving the segment in the series and ultimately the conical end segment. In this configuration, the interface segment, each telescoping segment and the conical end segment, each include a smaller outer diameter than the preceding segment. According to embodiments of the present invention, each segment can comprise a locking segment for locking each segment, or a group of series of segments, in the extended position by rotating the extended segment relative to the preceding segment.

According to other embodiments of the present invention, an adjustable length rear tip extender can comprise a fluted rear tip extender comprising a conical end segment, an interface segment and a plurality of conical intermediate segments. As with the telescoping rear tip extender, the interface segment of the fluted rear tip defines a receiving port for receiving the mounting nub at the rear of an inflatable cylinder and operably linking the fluted rear tip extender to the inflatable cylinder. The plurality of conical intermediate segments are arranged in an end-to-end configuration with each intermediate segment comprising a tab operably linking each conical end segment to the preceding conical intermediate segment. Similarly, the conical end segment further comprises a tab operably linking the conical end segment to the series of conical intermediate segments. The effective length of the fluted rear tip can be changed by cutting along a tab between a pair of conical intermediate segments, a conical intermediate segment or a conical end segment, or a conical intermediate segment and the interface segment. The conical intermediate segments comprise a conical shape such that regardless of the effective length chosen, the effective end of the fluted rear tip will have a rounded shape. According to embodiments of the present invention, the fluted rear tip comprises a plurality of frustoconical intermediate segments wherein the narrow end of each intermediate segment is affixed to the wide end of the next intermediate segment. In either embodiment of the fluted rear tip, the entire fluted rear tip can be molded as a single piece.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE FIGURES

The invention can be completely understood in consideration of the following detailed description of various embodiments of the invention in connection with the accompanying drawings, in which:

FIG. 1 shows an implantable penile prosthesis in accordance with embodiments of the present invention.

FIG. 2 shows an inflated implantable penile prosthesis in accordance with embodiments of the present invention.

FIG. 3 shows a deflated implantable penile prosthesis in accordance with embodiments of the present invention.

FIGS. 7-8 show a fluted rear tip extender in accordance with embodiments of the present invention.

FIG. 9 shows a trimmed or shortened fluted rear tip extender of FIGS. 7-8 in accordance with embodiments of the present invention.

Figures 4A, 4B, 4C, 4D:
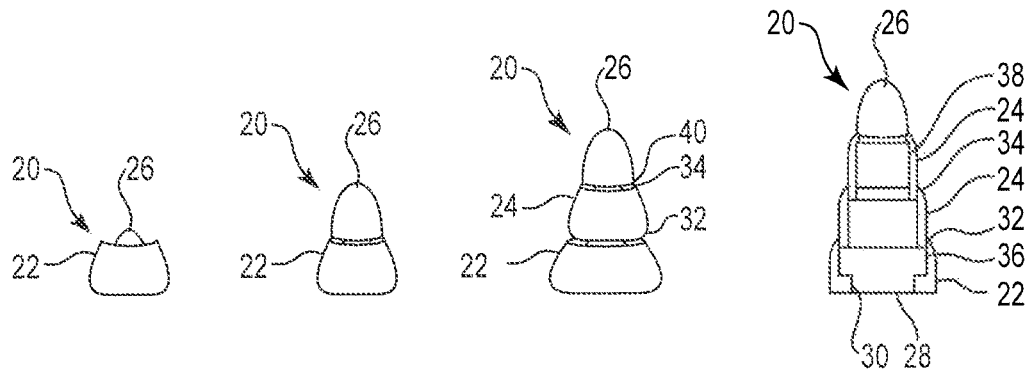
FIGS. 4a-4c show a telescoping rear tip extender being is stages of telescoping extension in accordance with embodiments of the present invention.
FIG. 4d shows a schematic cross-sectional view of the telescoping rear tip extender of FIG. 4c in accordance with embodiments of the present invention

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE FIGURES

Referring generally to FIGS. 1-3, an implantable penile prosthesis system 2, according to embodiments of the present invention, comprises one or more inflatable cylinders 4 (e.g., 2 adjacent cylinders) each operably linked to an inflating apparatus or reservoir 6 via one or more fluid conduits or connectors 8. The one or more inflatable cylinders 4 further include an inflatable portion 10 and a rear tip portion 12. The one or more inflatable cylinders 4 can include a valve 14 (e.g., one-way) switchable between a first position wherein fluid can only enter the inflatable cylinders 4 via the fluid connectors 8 and a second position wherein fluid can only leave the inflatable cylinders 4, also via the fluid connectors 8. In certain embodiments, the rear tip 12 can further include a locking mechanism or device. The inflating apparatus 6 can include a pump 18 that can be actuated to feed an inflation fluid through the one or more fluid connectors 8 and into the inflatable portion 10 of the one or more inflatable cylinders 4.

In general operation, the one or more inflatable cylinders 4 are surgically positioned within the corpus cavernosum of the penis with the inflating apparatus 6 positioned within the scrotum. The patient can actuate the pump 18 of the inflating apparatus 6 to force fluid through the fluid connector 8 into the inflatable portion 10 of the inflatable cylinder 4 causing the inflatable cylinder 4 to inflate. According to embodiments of the present invention, the valve 14 is biased into the first position so as to only permit fluid to enter the inflatable cylinder 4, wherein the valve 14 must be manually actuated to the second position by the patient to permit fluid to leave the inflatable cylinder 4 and deflate the inflatable portion 10. Actuating the valve 14 to the second position drains the inflating fluid from the inflatable cylinder 4 and returns the inflating fluid to the inflating apparatus 6.

Referring generally to FIGS. 4a-4d, the implantable penile prosthesis 2 can comprise a telescoping rear tip extender 20 affixable to the rear tip 12 of each inflatable cylinder 4. The telescoping rear tip extender 20 comprises an interface segment 22, at least one telescoping segment 24 and a generally rounded conical end segment 26. The interface segment 22 defines a receiving port 28 having a shoulder 30 for engaging a locking feature 16 of the inflatable cylinder 4. The locking feature can 16 include a locking nub. In other embodiments, the locking feature 16 can include a snap-fit portion, detent mechanism or feature, threading portion, and the like. Each telescoping segment 24 can include a first end 32 and a second end 34, wherein the diameter of the telescoping segment 24 is greater at the first end 32 than the second end 34 so as to define a generally frustoconical shape. The conical end segment 26 defines a generally conical shape and is adapted to brace against the pelvic bone to stabilize the implantable penile prosthesis. The telescoping segments 24 are arranged in an end-to-end configuration where the smaller second end 34 of each telescoping segment 24 interfaces with the larger first end 32 of the next telescoping segment 24. The conical end segment 26 is adapted to interface with the second end 34 of the last telescoping segment 24, while the interface segment 22 is adapted to interface with the first end 34 of the first telescoping segment 24.

According to embodiments of the present invention, the telescoping segments 24 and the conical end segment 26 are adapted to collapse partially or entirely into the interface segment 22 to shorten the effective length of the rear tip extender. Similarly, the telescoping segments 24 and the conical end segment 26 are adapted to extend partially or entirely from the interface segment 22 to increase the effective length of the rear tip extender. In this configuration, the interface segment 22 defines a bore 36 for receiving the telescoping segments 24 and the conical end segment 26.

Similarly, the telescoping segments 24 each define a bore 38 sized to receive the next telescoping segment 24. In this configuration, the telescoping segments 24 each define a smaller maximum outer diameter than the preceding telescoping segment 24, with the conical end segment 26 having the smallest outer diameter of any of the segments.

In embodiments of the present invention, the interface segment 22, the telescoping segments 24 and the conical end segment 26 can each include a locking mechanism or assembly 40. The locking assembly 40 is adapted to lock the segments in an extended position by twisting the segment relative to the preceding segment to engage the locking assembly 40. The locking assembly 40 can comprise a threaded assembly, a locking ring, a detent mechanism, a snap-fit feature, a press-fit feature and other means of locking the segments in the extended position. The interface segment 22, the telescoping segments 24, and the conical end segment 26 can be provided as individual segments in a kit, wherein medical room personnel can select the appropriate number of segments to achieve the desired overall length of the telescoping rear tip extender 20. While the telescoping extender 20 is generally depicted with three extending or distinct segments for adjusting rear tip extender lengths, embodiments can include numerous configurations, with additional (e.g., 4, 5, 6, . . . ), or fewer (e.g., 2), distinct telescoping segments to define the available lengths for the extender 20. Further, the segments 22, 24 can be configured in various sizes. For instance, certain embodiments can provide segments 0.5 or 1.0 cm in height such that telescoping adjustment lengthens the extender 20 in 0.5 or 1.0 cm increments. Other size and increment options are obviously available as well.

Figure 5:
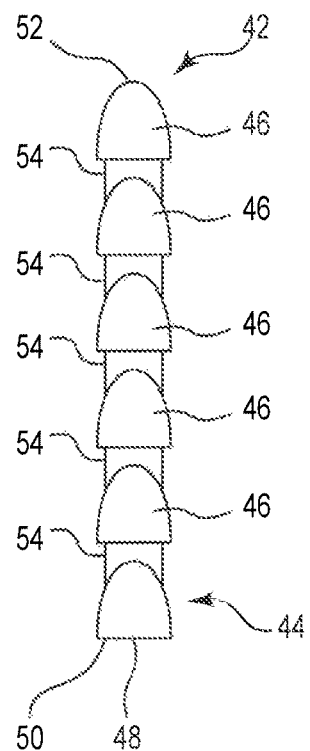
FIG. 5 shows a fluted rear tip extender having intermediate tabs in accordance with embodiments of the present invention.
Figure 6:
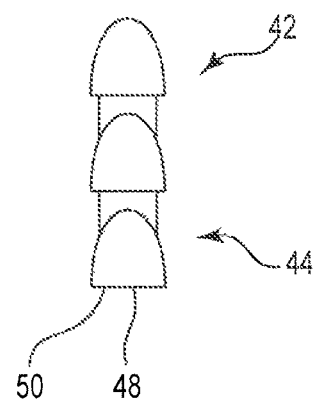
FIG. 6 shows a trimmed or shortened fluted rear tip extender of FIG. 5 in accordance with embodiments of the present invention.

Referring to FIGS. 5-6, embodiments of the implantable penile prosthesis 2 can include a fluted rear tip extender 42 affixable to the rear tip 12 of each inflatable cylinder 4. The fluted rear tip extender 42 further comprises an interface segment 44 and a plurality of conical segments 46. The interface segment 44 can include a receiving port 48 having a mating feature 50, such as a shoulder, for engaging the locking feature 16 (e.g., locking nub) of the inflatable cylindrical 4 or rear tip 12. Each of the conical segments 46 comprises a generally rounded conical tip 52 adapted to brace the rear tip extender 42 against the pelvic bone and tab 54 extending outwardly from the rear of the conical tip 52.

The conical segments 46 are arranged in an end-to-end configuration with the tab 54 of each conical segment 46 being affixed to the conical tip 52 of the preceding conical segment 46, with the final tab 54 of the last conical segment 46 being affixed to the interface segment 44. In operation, a user or physician can cut across the tab 54 to shorten the length of the rear tip extender 42 and expose the conical tip 52 below or preceding the cut tab 54. The length of each conical segment 46 from the tip 52 to end of the tab 54 can be a suitable length such as, for example, 0.5 cm such that removing each conical segment 46 from the fluted rear tip extender 42 shortens the effective length of the fluted rear tip extender 42 by 0.5 cm. For example, in certain embodiments, the overall length from the interface segment 44 to the tip 52 of an uncut or unaltered extender 42 can be from 1.0 cm to over 20.0 cm. FIG. 6 shows an embodiment of the fluted extender 42 of FIG. 5 cut or otherwise reduced in overall length to include three distinct segments, e.g., one interface segment 44 and two conical segments 46.

Figure 7:
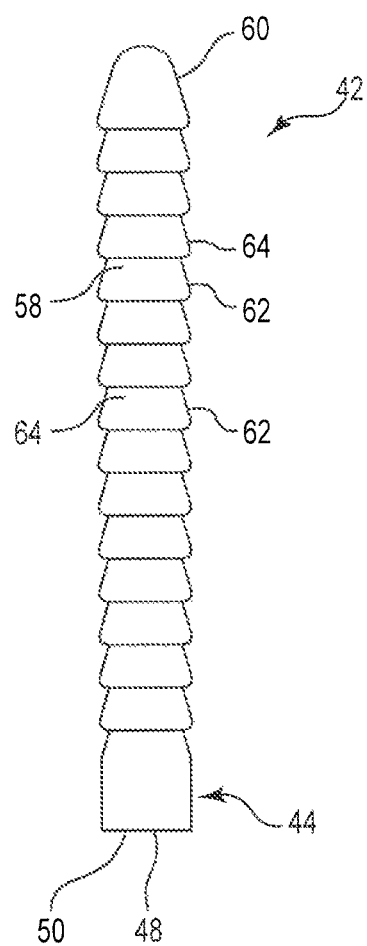

As shown in FIGS. 7-9, according to an embodiment of the present invention, the fluted rear tip extender 42 can alternatively comprise frustoconical intermediate segments 58 and a conical end segment or tip 60 instead of a plurality of conical segments 46. Each frustoconical segment 58 comprises a first end 62 and second end 64, wherein the outer diameter of the frustoconical segment 58 is greater than the outer diameter at the second end 64. As with the conical segments 46, the frustoconical segments 58 are arranged in an end-to-end configuration. However, unlike the conical segments 46, the second end 64 of each frustoconical segment 58 can be adapted to interface directly with the first end 62 of the next frustoconical segment 58. As a result, the effective length of the fluted rear tip extender 42 with frustoconical intermediate segments 58 is changed by cutting between the frustoconical segments 58 rather than along the tabs 54. In certain embodiments, the conical end segment 60 is selectively affixed (e.g., snap-fit, press-fit, etc.) to the second end 64 of the last frustoconical segment 58, while the interface segment 44 is affixed to the first end 62 of the first frustoconical segment 58. In other embodiments, the interface segment 44 can be selectively affixed (e.g., snap-fit, press-fit, threaded, etc.) to or in the first end 62 of the first segment 58. FIG. 9 shows an embodiment of the fluted extender 42 of FIG. 7 cut or otherwise reduced in overall length to include six distinct segments, e.g., one interface segment 44, four segments 58 and the tip 60.

Various embodiments of the fluted rear tip extender 42 can be molded as a single piece from a suitable polymer material. As a result, the fluted rear tip extender 42 saves considerable manufacturing cost as only a single mold is required to produce the fluted rear tip extender 42, while still providing the flexibility to change the effective length of the rear tip extender 42 as required.

In certain embodiments of the extenders 20, 42, portions or segments can include indicia or other markings to indicate various effective lengths for the extender 42, e.g., if cut down or at that particular segment for implantation. Indicia can also be provided to indicate cut or break lines to shorten the overall length of the extenders. Further, cutting off excess length can include trimming end regions of the cut segments or tabs (e.g., tabs 54) to provide the desired surface contour or consistency for the corresponding segment or tip.

The penile prosthesis 2, features, devices, structures and methods detailed herein are envisioned for use with many known penile prosthesis implants and systems (e.g., for male and female), features and methods, including those disclosed in U.S. Pat. Nos. 8,052,594, 7,169,103, 6,808,489 and 5,263,981. Accordingly, the above-identified disclosures are fully incorporated herein by reference in their entirety.

Generally, a method for implanting the penile prosthesis 2 having the telescoping rear tip extender 20 into a patient's body comprises making an incision in the patient's body proximate to the patient's corpus cavernosum. The one or more inflatable cylinders 4 are then inserted into the corpus cavernosum. The telescoping rear tip extender 20 is fitted to the rear tip 12 of the inflatable cylinder 4, e.g., snap-fit, nub elements, detents, threading, and the like. The telescoping rear tip extender 20 is extended until the conical end segment 26 abuts the patient's pelvic bone to achieve the desired length for the extender 20 and the effective overall length of the prosthesis 2 according to the individual anatomy of the patient. In other embodiments, the telescoping rear tip extender 20 is extended to the proper length prior to attachment to the inflatable cylinder 4.

Similarly, a method for implanting the implantable penile prosthesis 2 having the fluted rear tip extender 42 also comprises making an incision in the patient's body proximate to the patient's corpus cavernosum. The one or more implantable cylinders 4 are then inserted into the corpus cavernosum. The fluted rear tip extender 42 is then cut to shorten the extender 42 to the appropriate length in accordance with the patient's anatomical length, such that the end of the fluted rear tip extender 42 abuts against the pelvic bone while properly aligning the implantable cylinders 4 within the corpus cavernosum.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed:

1. A penile prosthesis system, comprising:
   at least one inflatable cylinder having a rear tip portion; and
   a fluted rear tip extender attachable to the rear tip portion of the at least one inflatable cylinder, the rear tip extender having a conical end segment, a plurality of generally frustoconical segments in serial alignment, and a base interface segment, the base interface segment configured to be attached to the rear tip portion of the at least one inflatable cylinder,
   each of the plurality of generally frustoconical segments having a first flared end and a second distal end, the plurality of frustoconical segments being integrally formed and substantially the same shape such that the second distal end of one of the plurality of frustoconical segments directly interfaces with the first flared end of another of the plurality of frustoconical segments, each of the plurality of frustoconical segments having a marking indicative of an effective length of the rear tip extender,
   the plurality of frustoconical segments including a first end frustoconical segment coupled to the base interface segment, one or more intermediate frustoconical segments, and a second end frustoconical segment removably coupled to the conical end segment,
   wherein the fluted rear tip extender is molded as a single piece from a polymer material,
   wherein the second end frustoconical segment can be removed from the fluted rear tip extender by cutting between segments, and one of the intermediate frustoconical segments can be coupled to the conical end segment to shorten the effective length of the rear tip extender.

2. The system of claim 1, further including a fluid reservoir and a pump device, wherein the fluid reservoir, pump device, and the at least one inflatable cylinder are in fluid communication via one or more conduits.

3. The system of claim 1, wherein the plurality of generally frustoconical segments includes five or more generally frustoconical segments.

4. The system of claim 1, wherein the base interface segment includes an engagement feature to facilitate attachment of the rear tip extender to the rear tip portion of the at least one inflatable cylinder.

5. The system of claim 1, wherein the conical end segment is configured to brace against a pelvic bone.

6. A penile prosthesis system, comprising:
   at least one inflatable cylinder having a rear tip portion; and
   a fluted rear tip extender attachable to the rear tip portion of the at least one inflatable cylinder, the rear tip extender having a conical end segment, a plurality of integrally formed generally tapered segments in serial alignment, substantially the same shape, and having a first flared end and a second distal end such that the second distal end of one of the plurality of tapered segments directly interfaces with the first flared end of another of the plurality of tapered segments, the rear tip extender including a base interface segment configured to be attached to the rear tip portion of the at least one inflatable cylinder, each of the plurality of tapered segments having a marking indicative of an effective length of the rear tip extender,
   the plurality of tapered segments including a first end tapered segment coupled to the base interface segment, a plurality of intermediate tapered segments, and a second end tapered segment removably coupled to the conical end segment,
   wherein the fluted rear tip extender is molded as a single piece from a polymer material,
   wherein the second end tapered segment and one or more of the plurality of intermediate tapered segments can be removed by cutting between segments, and the second distal end of an unremoved intermediate tapered segment can be coupled to the conical end segment to shorten the effective length of the rear tip extender.

7. The system of claim 6, further including a fluid reservoir and a pump device, wherein the fluid reservoir, pump device, and the at least one inflatable cylinder are in fluid communication via one or more conduits.

8. The system of claim 6, wherein the plurality of tapered segments includes five or more generally tapered segments.

9. The system of claim 6, wherein the plurality of tapered segments are frustoconical.

* * * * *